United States Patent [19]

Lenoir et al.

[11] 4,141,734
[45] Feb. 27, 1979

[54] PHOTOGRAPHIC DEVELOPING PROCESS

[75] Inventors: John Lenoir; Max Marthaler, both of Marly, Switzerland

[73] Assignee: Ciba-Geiby AG, Basel, Switzerland

[21] Appl. No.: 856,389

[22] Filed: Dec. 1, 1977

Related U.S. Application Data

[63] Continuation-in-part of Ser. No. 719,621, Sep. 1, 1976, abandoned.

[30] Foreign Application Priority Data

Sep. 11, 1975 [CH] Switzerland ............... 11814/75

[51] Int. Cl.$^2$ ............... G03C 7/00; G03C 5/38; G03C 5/30
[52] U.S. Cl. ............... 96/53; 96/61 M; 96/66.4
[58] Field of Search ............... 96/61 M, 53, 66, 66.3, 96/66.4, 66.5, 50, 29 R

[56] References Cited

U.S. PATENT DOCUMENTS

| | | | |
|---|---|---|---|
| 2,935,404 | 5/1960 | Dersch | 96/66.5 |
| 3,419,392 | 12/1968 | Thompson | 96/66.3 |
| 3,447,925 | 6/1969 | Dersch | 96/66.5 |

*Primary Examiner*—Mary F. Kelley
*Attorney, Agent, or Firm*—Sprung, Felfe, Horn, Lynch & Kramer

[57] ABSTRACT

A process for developing photographic silver halide material, which has been exposed image-wise is provided. The aqueous developer preparation used contains a developer compound for the silver halide, a water-soluble solvent for the silver halide and an aliphatic, cycloaliphatic, aromatic or heterocyclic di- or trisulphide. These preparations remain clear over a long period of time during which they do not lose their effectiveness by becoming turbid or by sedimentation of silver. They are of special advantage in continuously operated photographic developing processes.

18 Claims, No Drawings

PHOTOGRAPHIC DEVELOPING PROCESS

This is a continuation-in-part application of the co-pending application Ser. No. 719,621, filed Sept. 1, 1976 now abandoned.

When photographic materials which contain at least one layer which contains a silver halide are processed, the silver developing is usually carried out in the presence of so-called developer substances, such as dihydroxybenzenes, aminophenols, diaminobenzenes, pyrazolidones, reductones or hydroxylamine derivatives. Developing is in the main carried out in an alkaline medium and the developer solution in most cases also contains further additives, such as salts of sulphurous acid for stabilising, buffer substances and antifogging agents. However, it is also possible for some of these substances to be contained in the photographic material. In order to achieve special results, it is also known to develop photographic material in the presence of solvents for silver halides. For this purpose, organic compounds of divalent sulphur, such as, say, mercapto compounds, thioethers or thioamides, salts of thiocyanic acid or salts of sulphurous acid in high concentration, especially salts of thiosulphuric acid are employed. Developers containing such additives are known as fine grain developers and internal grain developers. (See E. Mutter, "Die Technik der Negativ- und Positivverfahren" ("The Technology of Negative and Positive Processes"), Springer 1955, page 158 to 159). The developing of latent silver nuclei inside the grains is of particular importance in the case of reversal development processes, in which salts of thiocyanic acid are frequently added to the first developer. Further important embodiments of this type are the monobaths, such as are described in say, U.S. Pat. No. 3,857,710 or by G. Haist in "Monobath Manual", Morgan 1960. However, many of these developers have the disadvantage that they more or less rapidly reduce the silver halide dissolved out of the photographic material. As a result of this, the developer becomes turbid and after some time a sediment of silver forms and this is able to adhere both to the photographic material and to parts of the developing equipment. The formation of this sediment proves to be particularly disadvantageous in equipment which operates continuously. In German Offenlegungsschrift No. 2,437,353, derivatives of 1-phenyl-5-mercaptotetrazole are proposed in the developer for X-ray film to counter the deposition of silver in developing equipment. In U.S. Pat. No. 3,173,789 and in German Auslegeschrift No. 1,175,077, heterocyclic mercapto compounds are described as additives in processing solutions for combating the formation of a silver sediment and in German Offenlegungsschrift No. 1,909,743 aliphatic mercaptocarboxylic acids are described as such additives. In U.S. Pat. No. 3,318,701, α-liponic acid is proposed to counter the formation of a sediment and in German Offenlegungsschrift No. 2,040,801 4-acylamino-1,2,3-triazoline-5-thiones are proposed for this purpose. These subtances are usually employed in amounts of between 5 and 5,000 mg per liter of developer solution.

It has been found that the proposed additives are able to delay the formation of a silver sediment over a more or less lengthy period but they display diverse undesirable side effects. Substances which have a good clarity-preserving effect have a considerable influence on the properties of the developers. In the case of multi-layer colour materials the main effect is to reduce the sensitivity of the uppermost layer. In the case of masking developing of silver dye-bleach materials, impairment of the masking effect arises. Other substances are unstable in the developer, rapidly lose their effectiveness due to atmospheric oxidation or decompose with the formation of secondary products which are malodorous and/or harmful to health. All of these disadvantages make it vastly more difficult to use the clarity-preserving substances proposed hitherto in practice and in many cases make such use impossible.

The object of the present invention is to find a developing process and a developer which can be used without having an adverse effect on developing, in the presence of a solvent for silver halides, and without the disadvantageous side effects which have been mentioned. Surprisingly, this object has been achieved with the aid of certain organic compounds which contain 2 to 3 sulphur atoms bonded to one another.

The use of organic disulphides in the field of photography is already known. Thus, according to U.S. Pat. No. 1,742,042 and U.S. Pat. Nos. 3,057,725 and 3,062,654, certain organic disulphides are used to stabilise silver halide emulsions. German Offenlegnungschrift No. 2,162,715 recommends the use of certain disulphides for stabilising the silver image in a silver complex transfer process, whilst in German Offenlegungsschrift No. 1,768,400 Bunte salts are recommended for this purpose. However, these applications have nothing to do with the use of the disulphides and trisulphides of the present invention in photographic developing processes.

The subject of the invention is a process for developing photographic material, which has been exposed image-wise, using an aqueous preparation which contains (a) a developer compound for the silver halide, (b) a water-soluble solvent for the silver halide and (c) a compound of divalent sulphur in solution, characterised in that this sulphur compound corresponds to the formula

wherein $m$ and $n$ each denote an integer with a value of 1 to 4, $p$ denotes 1 or 2, B and D each denote an aliphatic, cycloaliphatic, araliphatic, aromatic or heterocyclic radical and A and E each denote a radical of the formulae

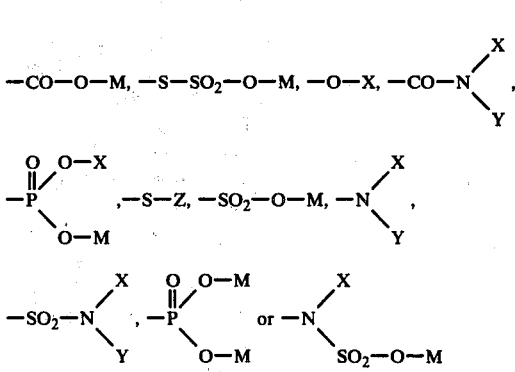

wherein X and Y in each case are hydrogen or alkyl which has at most 8 carbon atoms and is optionally substituted by hydroxyl groups, carboxylic acid groups or sulphonic acid groups and Y also represents a phenylsulphonic acid group, a lower alkylsulphonyl group or a phenylsulphonyl group and M represents a monovalent cation. Z has the meanings of X and Y except, however, for hydrogen.

The invention also relates to compositions or preparations for developing photographic material which contains a silver halide and has been exposed imagewise, which compositions or preparations contain the components (a), (b) and (c), wherein sulphur compounds of the formula (1) being used as component (c). These compositions can be in various forms, for example in the form of a mixture of solid components (a), (b) and (c), a concentrate (parts of a solvent may be present), a solution, emulsion, or suspension and as a rule are diluted to form aqueous solutions (baths) for the said developing of photographic materials. Solvents which are completely, sparingly or not soluble in water may be additionally used to form the baths. The compositions or preparations optionally contain further customary components. The concentrates may contain all components or only a part of them that is one or several of the concentrated components are separately stored. The concentrates are diluted or if in separate form mixed and then diluted in order to obtain the photographic developing baths.

The solvents which may be present in the concentrates are besides water e.g. glycols and glycol ethers such as (mono)methyl, ethyl, propyl or butyl ethers of ethylene glycol. Concentrates which contain only a part of the components (a), (b) and (c) and which are mixed and then diluted for preparing the photographic developing baths are preferred. In a typical example which is most frequently a two-package concentrate, such a first concentrate contains the developing agents, preferably a mixture of several substances (a) and the disulfide together with other compounds normally used in a developing mixture, such as stabilizers, hardeners, development accelerators etc. (c) while the water-soluble solvent for the silver halide and the remaining inorganic components form a second concentrate which may be either a solid or an aqueous concentrate. The developer / disulfide concentrate may contain e.g. 5 to 10%, preferably 7 to 10%, by weight of one or more developing agents, 0.1 to 2%, preferably 0.5 to 1.5% by weight of the disulfide, 40 to 90%, preferably 50 to 80% by weight of an ethylene glycol monoalkyl ether (monoethyl ether), the remainder to 100% being water with optionally further organic compounds dissolved therein. The first concentrate is preferably present as an aqueous one.

The second concentrate comprises an alkali metal or ammonium thiosulfate, for example sodium thiosulfate and as customary components, sodium sulphite and sodium carbonate and/or other buffering salts, such as sodium borate or sodium phosphate. This second concentrate is in a solid form or is present as an aqueous preparation. The amounts of the single components are e.g. about 0.1 to 10 or 20 to 50% by weight of the thiosulfate (sodium thiosulfate), the lower range being suitable for silver dye bleach masking developers as described in example 3 and the higher range being suitable for monobaths as described in examples 1 and 2; 20 to 50% by weight of sodium sulphite and/or sodium bisulphite, 5 to 30% by weight of sodium or potassium salts of carbonic, phosphoric or boric acid, the remainder to 100% being optionally water (when the concentrates are aqueous preparations).

Preferred compounds of the formula (1) can be represented by the following formulae:

(2)

(3)

(4)

(5)

(6)

(7)

(8)

(9)

(10)

(11)

(12)

(13)

(14)

-continued

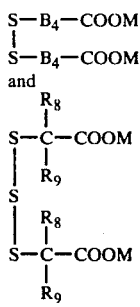

In the formulae (2) to (16) identical symbols always have the same meaning: $A_1$ and $E_1$ independently of one another denote a radical of the formulae

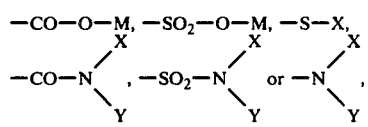

$A_2$ and $E_2$ independently of one another denote a radical of the formulae

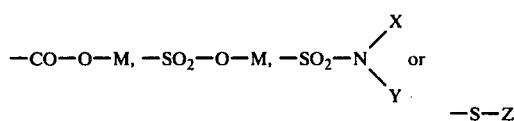

and $A_3$ denotes a radical of the formulae

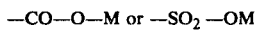

in which formulae M, X and Y have the indicated meanings; $B_1$ and $D_1$ independently of one another denote an aliphatic, cycloaliphatic or araliphatic radical or donote an aromatic or heterocyclic 5-membered or 6-membered ring which is optionally fused with a further benzene ring, and the hetero-ring contains 1 to 3, preferably 1 to 2, nitrogen atoms, an oxygen atom or a sulphur atom; $B_2$ denotes a saturated 3-membered to 8-membered, especially a 5-membered to 6-membered, isocyclic ring or an aromatic-isocyclic or aromatic-heterocyclic 6-membered ring in which the heterocyclic part contains nitrogen; $B_3$ denotes cyclopentyl which in the 1-position is bonded to the sulphur atom and in the 5-position is bonded via —CH$_2$— to the CO group, cyclohexyl which in the 1-position is bonded to the sulphur atom and in the 3-position or 4-position is bonded to the CO group, or phenyl which in the 1-position is bonded to the sulphur atom and in the 2-position or 4-position is bonded to the CO group; $B_4$ denotes optionally substituted pyrimidyl which in the 2-position is bonded to the sulphur atom and in the 5-position or 6-position is bonded to the CO group, or optionally substituted pyridinyl, which in the 2-position is bonded to the sulphur atom and in the 4-position or 5-position is bonded to the CO group; $R_1$ denotes hydrogen, optionally substituted alkyl with 1 to 6 carbon atoms, aralkyl, cycloalkyl, optionally substituted phenyl or a five-membered to six-membered hetero-ring which contains 1 to 3 nitrogen atoms or 1 oxygen atom or 1 sulphur atom, or denotes a carboxylic acid group; $R_2$ denotes a direct bond or optionally substituted alkylene, alkylidene, phenylene or aralkylene; $R_3$ denotes hydrogen or optionally substituted alkyl with 1 to 6 carbon atoms or alkenyl; $R_4$ denotes a direct bond or alkylene, preferably methylene or ethylene, and also ethylidene —CH(CH$_3$)—,

phenylene,

or —CONHCH$_2$—; $R_5$ denotes hydrogen, —CH$_3$, —CH$_2$OH, —COOH, —CH$_2$COOH, cyclohexyl or cyclopentyl, phenyl, substituted phenyl, furyl or thienyl, substituents on the phenyl ring being, for example, alkyl with 1 to 4 carbons atoms, preferably methyl, as well as halogen, preferably fluorine, chlorine or bromine, and also amino (—NH$_2$), sulphonic acid (—SO$_3$H) and, preferably, sulphonamide (—SO$_2$NH$_2$); $R_6$ denotes hydrogen, methyl or ethyl; $R_7$ denotes hydrogen, —CH$_3$, —CH$_2$COOH, phenyl, p-tolyl or p-benzenesulphonamide; $R_8$ and $R_9$ independently of one another denote hydrogen or —CH$_3$; M preferably denotes the hydrogen cation or an alkali metal cation, such as, for example, Na$\oplus$ or K$\oplus$; $m_1$ denotes the members 1, 2 or 3; $m_2$ denotes the numbers 1 or 2; $n_1$ denotes the numbers 1, 2 or 3; $p$ denotes the numbers 1 or 2 and $t$ denotes the numbers 1, 2, 3 or 4.

A large number of the organic disulphides and trisulphides to be used according to the invention are known; any siulphides which are not yet known can be manufactured according to methods which are in themselves known and, in the case of the disulphides, the oxidation of the corresponding mercaptans (A. Schöberl in Methoden der organischen Chemie (Methods of Organic Chemistry), Houben-Weyl, volume 9, page 59 (1956) or of the corresponding Bunte salts (H. Distler, Angew. Chem. 79, 720 (1967)) is particularly important. The latter reaction is suitable, for example, for the manufacture of asymmetric disulphides.

Trisulphides can be manufactured, for example, by reacting a Bunte salt with sodium sulphide in accordance with the method of Swan and Milligan, J. Chem. Soc. 1963, 3,608.

$\beta, \beta'$-Dithiodicarboxylic acids, their derivatives and similar compounds can also be obtained direct from the corresponding $\alpha, \beta$-unsaturated carboxylic acids and sodium tetrasulphide, in accordance with U.S. Pat. No. 2,623,066.

A preferred manufacturing process for dithiodicarboxylic acids, especially for $\beta,\beta'$-dithiodicarboxylic acids, is the reaction of an $\alpha,\beta$-unsaturated carboxylic acid, or its derivatives, especially the alkyl esters, preferably the methyl or ethyl esters, in accordance with the following equations:

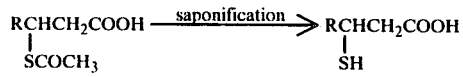

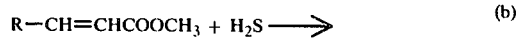

-continued

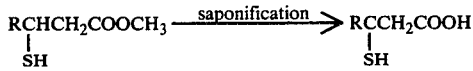

The mercapto compounds obtained according to (a) or (b) can then be converted into disulphides by oxidation.

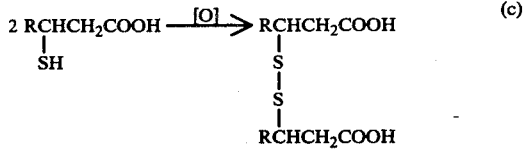

Suitable compounds for carrying out this process are, for example, the following unsaturated acids and their derivatives: acrylic acid, methacrylic acid, acrylonitrile, crotonic acid, 2- and 3-pentenoic acid, isopropylidenemalonic acid, itaconic acid, maleic anhydride, crotononitrile, vinylacetic acid, citraconic acid, ethyl propiolate, mesaconic acid, allylacetic acid, 3,3-dimethylacrylic acid, tiglic acid, allylthioacetic acid, trans-aconitic acid, diethyl glutaconate, 2-hexenedioic acid dinitrile, allylmalonic acid, diethyl allylmalonate, 3-hexenedioic acid, 2-hexenoic acid, 3-cyclohexene-1-carboxylic acid, 6-heptenoic acid, cinnamic acid, methyl cinnamate, ethyl cinnamate, α-methylcinnamic acid, 4-methylcinnamic acid, 2-, 3- or 4-methoxycinnamic acid, 4-hydroxycinnamic acid, d4-chlorocinnamic acid, 4-sulphamoylcinnamic acid, 3-hydroxy-4-methoxycinnamic acid, ethyl 4-sulphocinnamate, 2-carboxycinnamic acid, 3,4-methylendioxycinnamic acid, 2,3-or 3,4-dimethoxycinnamic acid, 3(2'-furyl)-acrylic acid, 3(2'-thienyl)-acrylic acid, 3(3'-pyridyl)-acrylic acid, 3(2'-pyridyl)-acrylic acid, 3(4'-pyridyl)-acrylic acid, 5-norbordnene-2-acrylic acid, 2-cyclopentenyl-1-acetic acid, 5-norbornene-2-carboxylic acid, bicyclo[2,2,2]-octane [7]-2,3,5,7-tetracarboxylic acid anhydride, methyl 2-nonenoate, ethyl phenylpropiolate, diethyl diallylmalonate, styrylacetic acid, 4-cyclooctene-1-carboxylic acid, 4-cycloheptene-1-carboxylic acid and 4,4'-diamino-stilbene-3,3'-dicarboxylic acid.

The disulphides and trisulphides which follow may be mentioned as examples: 2,2'-dithio-diethanesulphonic acid, di-potassium 3,3'-dithio-dipropanesulphonate, di-potassium 2,2'-dithio-dipropanesulphonate, di-guanidinium 4,4'-dithiodibutanesulphonate, di-sodium 3,3'-dithio-dibutanesulphonate, di-sodium 3,3'-dithio-3,3-dimethyl-dibutanedisulphonate, disodium 5,5'-dithio-dipentanedisulphonate, di-guanidinium 4,4'-dithio-dihexanedisulphonate, di-guanidinium 6,6'-dithiodihexanedisulphonate, 4,4'-diphenyl-disulphide-disulphonic acid, di-sodium 2,2'-dibenzyl-disulphide-disulphonate, 8,8'-diquinoline-disulphide-5,5'-disulphonic acid, 4,4'-bis-(methylsulphonyl)-diphenyl disulphide, 2,2'-dithio-diethanesulphonamide, 2,2'-bis-(methanesulphonamide)-diethyl disulphide, 2,2'-diethoxy-diethyl disulphide, 2,2'-dihydroxyethyl disulphide, 2,2'-bis-(ethylamino)-ethyl disulphide, 2,2'-bis(2''-hydroxyethylamino)-ethyl disulphide, 4,4'-pyridyl disulphide, 2,2'-diaminodiphenyl disulphide, 4,4'-dihydroxydiphenyl disulphide, 2,2'-dithio-diphenyldicarboxylic acid (dithiodisalicylic acid), 3,3'-dithio-diphenyldicarboxylic acid, 4,4'-dithio-diphenyldicarboxylic acid, 5,5'-dithiobis-[2-hydroxy]-benzoic acid, 2,2'-dithio-diglycollic acid, 3,3'-dithio-dipropionic acid, 2,2'-dithio-dipropionic acid, 2,2'-dithiodibutyric acid, 3,3'-dithiodibutyric acid, 4,4'-dithiodibutyric acid, 2,2'-dithiodiisobutyric acid, 2,2'-trithio-diisobutyric acid, dithiodipivalic acid, dithiodipivalic acid diamide, 3,3'-dithiobis-(2,2'-diamino-2,2'-dimethyl)-propionic acid, 3,3'-dithio-bis-(3,3'-dimethyl)-butyric acid, 4,4'-dithio-bis-(3,3'-dimethyl)-2-hydroxybutyric acid, dithio-bis-succinic acid, dithio-bis-malonic acid, dithiodiitamalic acid, 2,2'-dithio-bis-(2,2'-diphenyl)-acetic acid, 3,3'-dithio-bis-(3,3'-diphenyl)-propionic acid, 3,3'-dithio-bis-[3,3'-di-(4''-sulphophenyl)]-propionic acid, 3,3'-dithio-bis-[3,3'-di-(4''-tolyl)]-propionic acid, 3,3'-dithio-bis-[3,3'-di-(4''-sulphamoyl-phenyl)]-propionic acid, 4,4'-dithio-bis-pyridine-3,3'-dicarboxylic acid, 6,6'-dithio-bis-dinicotinic acid, 4,4'-diamino 2,2'-dithio-bis-pyrimidyl-5,5'-dicarboxylic acid, cystine, 4,4'-dithio-divaleric acid, 5,5'-dithio-divaleric acid, 3,3'-dithio-divaleric acid, 4,4'-dithio-bis-[2,2-dimethyl]-valeric acid, 4,4'-dithio-bis-[4-methyl]-valeric acid, 6,6'-dithiodicaproic acid, 5,5'-dithiodicaproic acid, 2,2'-dithio-bis-dodecanoic acid, the disulphide of penicillinamine, 3,3'-dithio-bis-[2-methyl]-butyric acid, sodium 3,3'-dithiodiglutarate, 3,3'-dithio-diadipic acid, 3,3'-dithio-bis-[2'-cyclopropyl]-propionic acid, 3,3'- and 4,4'-dithio-dicyclohexanecarboxylic acid, 4,4'-dithio-bis-[cyclohexane-1,2-dicarboxylic acid], 5,5'-dithio-bis-[4-methylcyclohexanedicarboxylic acid], 3,3'-dithio-bis-(cyclopentyl)-acetic acid, N,N'-diacetyl-cystine, 3,3'-dithio-bis-[3-(2'-furyl)]-propionic acid, 3,3'-dithio-bis-[3-(2'-thienyl)]-propionic acid, 5,5'-dithio-bis-(4-methyl)-cyclohexane-1,2,3-tricarboxylic acid, monomethyl 3,3'-dithio-bis-propanephosphonate, 4,4'-dithio-bis-(4,5-dimethyl-caproic acid, 5,5'-dithio-bis-(4,5-dimethyl)-caproic acid, 4,4'-dithio-bis-(5-methyl)-caproic acid, 4,4'-dithio-dibutanephosphonic acid, 3,3'-dithio-dibutanephosphonic acid, the monoethyl ester of 3,3'-dithio-bis-(propanephosphonic acid), 3,3'-dithio-bis-(N,4''-sulphophenyl)-propionamide, 1,1'-dihydroxyethylmercapto-2,2'-dipropyl disulphide, 1,1'-bis-[(N,N-dihydroxyethyl)-amino]-2,2'-propyl disulphide, 1,1'-bis-[bis-(carboxyethylmercapto)]-3,3'-butyl disulphide, 2,2,5-trimethyl-3,4-dithioheptane-1,7-dicarboxylic acid, 2-methyl-3,4-dithio-heptane-1,7-disulphonic acid, 2,2'-dithiodipropionic acid N,N'-carboxymethylamide, trisulphide-acetic acid, dibenzyl-disulphide-4,4'-dicarboxylic acid, 4,4'-bis-(carboxymethylmercapto)-diphenyl disulphide, 1,1'-bis-[2''-carboxyethylmercapto]-2,2'-diethyl disulphide and 2,2'-dithio-bis-[2-benzimidazole-6-sulphonic acid]-ethane.

The new disulphides of the formula

wherein $A_4$ denotes a radical of the formulae —CO—O—M, $SO_2$—O—M or —S—$Z_1$, in which M is a monovalent cation and $Z_1$ is alkyl which has at most 8 carbon atoms and is optionally substituted by hydroxyl groups, carboxylic acid groups or sulphonic acid groups, $B_5$ denotes a cyclohexane radical which is bonded in the 1-position to the sulphur atom and the 3- or 4-position to the —CO— group and which is optionally further substituted, and $m_2$ denotes the number 1 or 2, prove to be particularly advantageous.

Further new and suitable disulphides correspond to the formula

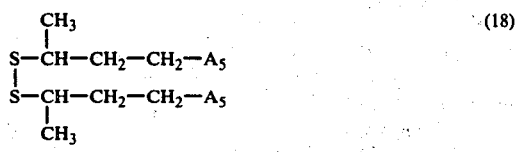

wherein $A_5$ is a radical of the formulae

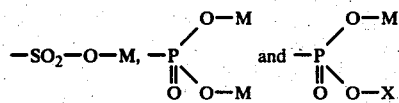

and M and X have the indicating meanings.

The compounds of the formula (17) and (18) can be manufactured by the methods which have been mentioned and are in themselves known, for example by first reacting a $\beta,\gamma$-unsaturarted homocyclic or aliphatic halogen compound with an alkali metal sulphite or mercaptide, or with a trialkyl phosphite. The reaction product is then treated with hydrogen sulphide or thioacetic acid in the presence or the absence of catalysts. Any ester groups which may be present in the reaction product are saponified and the resulting mercaptan is oxidised. Oxidising agents which can be used are, for example, iodine, hydrogen peroxide and salts of trivalent iron, but especially oxygen in the presence of metal ions as catalysts.

The disulphides can also be manufactured by alkylation or arylation of alkali metal disulphides, especially with a suitable alkylating agent or arylating agent. Furthermore, it is also possible to manufacture the corresponding mercaptan by alkylation of an alkali metal hydrogen sulphide or by alkylation of thiourea and subsequent saponification and subsequently to oxidise the mercaptan.

In the forefront of the alkylating agents are halogenated compounds, especially chlorine and bromine compounds, and also sulphonic acid ester, sultones, lactones, episulphides, epihalogenohydrins and epoxides. Examples of typical starting materials are: ethylene oxide, 2-bromoethanesulphonic acid, 2-chloroethanesulphonic acid, diethyl chloromethanephosphonate, 2-chloroethanol, chloroacetic acid, ethylene sulphide, 3-bromopropanesulphonic acid, 2-bromopropanesulphonic acid, 2-bromopropionyl chloride, 3-chloropropionic acid N-(3-sulphophenyl)-amide, allyl chloride, allyl bromide, propylene oxide, epichlorohydrin, propylene sulphide, propanesultone, 2,2'-dithio-bis-(1-bromo)-propane and 1,1'-dithiobis-(2-bromo)-propane, propiolactone, 4-butyrolactone, 2-, 3- or 4-chlorobutyric acid, ethyl-2-chlorobutyrate, 3-butanesultone, 4-butanesultone, 4-chlorobutane-sulphochloride, 4-chlorobutyric acid N-(4'-sulphophenyl)-amide, $\alpha$-bromo-p-toluic acid, $\alpha$-bromo-p-toluenesulphonyl chloride, ethyl $\alpha$-bromoisobutyrate, chloropivalic acid, dimethyl bromomalonate, 2- or 4-chloro-nitrobenzene, 2-chloro-5-nitrobenzenesulphonic acid, 3-chloro-2-hydroxy-propionic acid and 4-bromo-4-phenylbutyric acid.

The aqueous preparations to be used according to the invention for developing a photographic material which has been exposed image-wise can, in other respects, contain components which are in themselves known.

They preferably contain as component (a), customary developer substances for silver halides, for example dihydroxybenzenes, aminophenols, diaminobenzenes, pyrazolidones, reductones or hydroxylamine derivatives.

Customary water-soluble solvents, for silver halides, as component (b) are, for example, mercapto compounds, thioethers or thioamides, salts of thiocyanic acid, salts of sulphurous acid (sulphites) in high concentration and, preferably, salts of thiosulphuric acid (thiosulphates). In the aqueous formulations, the sulphites can be employed, for example, as a rule in an amount of more than 20 g/l, but optionally also in smaller amounts, such as, for example, 10 to 20 g/l, and the thiocyanates and thiosulphates can be employed in a concentration of 0.2 to 10 g/l.

The concentration of the thiosulphate is advantageously 10 to 200 g/l when it is used in a monobath and 0.1 to 10 g/l in masking developers for silver dye-bleach material. Suitable sulphur compounds are, above all, those of the formulae (5) to (18). The sulphur compounds can also be used in developer formulations for reversal, chromogenous, X-ray or black-and-white film materials.

The sulphur compounds of the formulae (1) to (18) form component (c). They can be added in amounts of 0.05 to 10 g/l, preferably 1 to 4 g/l, to the aqueous developer preparation.

A very particularly valuable application of the present process is the developing, with a developer formulation of the indicated composition, of silver dye-bleach material which has a composition suitable for reducing undesirable secondary colour densities.

Preferably this relates to the process for the manufacture of masked subtractive positive colour images by the silver dye bleach process with subsequent exposure, silver developing dye-bleaching, silver bleaching and fixing steps. The process which allows the production of images with improved colour rendering is characterized by the use of a photographic material, which contains at least two different dyestuffs, each in a different layer, the absorption maximum of each of the said dyestuffs corresponding to one of the three primary colours red, green and blue and, allocated to each of the said dyestuffs, a silver halide emulsion sensitized to a specific range of the spectrum. The photographic material is further characterized by the fact that the silver halide emulsion allocated to one of the dyestuffs which has an undesirable secondary colour density to be compensated, at least partly consists of silver iodide, and in another layer there exists a second dyestuff, whose main colour absorption range corresponds to the secondary colour density of the first dyestuff, whereby at least one second silver halide emulsion is allocated to this second dyestuff, which silver halide emulsion is free from silver iodide.

At least one further layer, adjacent to that containing the second dyestuff and separated from the layer containing the first dyestuff contains colloidal nuclei, which are able to deposit metallic silver from soluble silver complexes. The process is further characterized by the fact, that the silver developing bath, with which the material is treated after exposure, contains a ligand which is able to form water-soluble silver complexes capable of diffusing into an adjacent layer. By addition of one of the compounds of formulae (1) to (18), formation of a metallic silver deposit in the developing bath can be avoided. Compounds which can be used are in particular those of formulae (8) to (18).

The disulphides and trisulphides to be used according to the invention are distinguished, inter alia, by the fact that they prevent the deposition of silver in developer solutions over an astonishingly long period.

In contrast to the atni-sediment agents used hitherto, the compounds used according to the invention are otherwise photographically virtually inactive and very stable under the customary conditions. By virtue of these properties, the amount of anti-sediment agent which is added can be selected as desired within very wide limits and this is especially important for the continuous procedure. In contrast to other sulphur compounds, the compounds to be used according to the invention do not cause any unacceptable troublesome odours.

Manufacturing instructions

A. 3,3'-Dithio-dibutyric acid (Compound 101)

40 ml of thioacetic acid are added to 43 g of crotonic acid in 100 ml of dioxane. After adding 20 mg of benzoyl peroxide, the mixture is kept at the boiling point under reflux for 6 hours. The solvent and the excess thioacetic acid are removed by distillation and the product is purified by vacuum distillation. 75 g (92% of theory) of 3-acetylmercapto-butyric acid are obtained; boiling point 94° to 95° C/0.45 mm Hg. $n_D^{20}$ 1.4908.

65 g of the product thus obtained are slowly added to 560 ml of a 2 N aqueous solution of sodium hydroxide. The mixture is stirred for a further 15 hours at room temperature and acidified with 50% strength sulphuric acid. The fee mercapto-acid is extracted with ether. After evaporating off the ether, the product is distilled. 41 g of 3-mercapto-butyric acid are obtained; boiling point 45° to 46° C/0.2 mm Hg. $n_D^{20}$ 1.4782.

12 g of 3-mercapto-butyric acid are dissolved in 200 ml of 2 N ammonium hydroxide solution. 2 ml of a 0.02 normal solution of copper-II sulphate are also added and the mixture is stirred intensively under an oxygen atmosphere. When oxidation has ended, the reaction solution is acidified and extracted with ether. The organic phase is evaporated and the residue is recrystallised from acetone and water.

Yield: 9.6 g of 3,3'-dithiodibutyric acid, white crystals with a melting point of 97° to 99° C.

B. 1,1'-Dithio-dicyclohexane-4,4'-dicarboxylic acid (Compound 107)

can be manufactured from 3-cyclohexene-1-carboxylic acid following manufacturing instruction A. A mixture of stereoisomers is obtained. Melting point 115° to 119° C and 160° to 170° C.

C. Disodium salt of 3,3'-dithiodibutane-1,1'-disulphonic acid (Compound 105)

26 g of 5-methyl-1,2-oxathiolane-2,2-dioxide (M. Robbins and C. Broadder, J. org. Chem. 39, 2,459 [1974]) are stirred in 100 ml of absolute ethanol with 14.5 g of thiourea for 20 hours under reflux. The reaction product is filtered off and dried. Yield: 34 g (84% of theory). Melting point: 255° C (decomposition). The product is then treated, in 250 ml of ethanol, with ammonia and the mixture is warmed under reflux for 1½ hours. After evaporating, the residue is recyrstallised from methanol and toluene. Yield: 22.3 g of guanidinum 3-mercaptobutanesulphonate, melting point 137° to 140° C.

4.6 g of this salt in 50 ml of 2 N ammonia solution and 2 ml of 0.02 normal copper sulphate solution are catalytically oxidised by oxygen. After concentrating and diluting again, the product is converted into its sodium salt using a cation exchanger and the salt is precipitated from the aqueous solution by adding isopropanol. After drying, 2.4 g of di-sodium 3,3'-dithio-dibutanesulphonate are obtained.

The other disulphides mentioned in the examples which follow have either been described in the literature or are manufactured according to similar instructions.

EXAMPLE 1

An aqueous monobath developer solution of the following composition is prepared:
Tetrasodium ethylenediaminetetraacetate: 2 g/l
Anhydrous sodium sulphite: 60 g/l
Anhydrous sodium carbonate: 25 g/l
85% strength potassium hydroxide: 7 g/l
1-Phenyl-3-pyrazolidone: 1 g/l
Hydroquinone: 16 g/l
Anhydrous sodium thiosulphate: 70 g/l The pH value of the solution is about 10.5. 2.4 g/l of 3,3'-dithiodibutyric acid of the formula

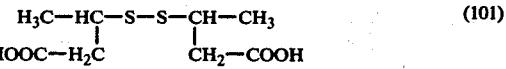

are added to a second solution, which otherwise has the same composition. 10 exposed 9 cm × 12 cm sheet films are trearted in succession, each for 8 minutes, at 24° C in 1 liter of each of these two developers. A black-and-white photographic film of medium sensitivity is used. The pieces of film are then washed.

A developer solution which contains dithiodibutyric acid and is used in this way is clear 2 hours after the treatment of the material has been concluded and no turbidity or deposition of a sediment can be observed even after 48 hours. A developer solution which had an otherwise identical composition, but without dithiodibutyric acid, and was used in the same way is turbid and opaque 2 hours after use; it clears after 24 hours but a grey-black precipitate has settled out.

The dithio compounds which follow can also be added, in 1/100 molar concentration, to the developer, in place of the dithiodibutyric acid of the formula (101).

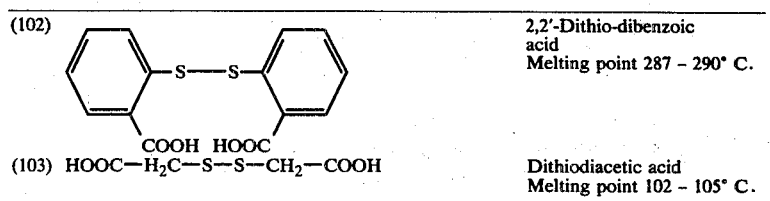

2,2'-Dithio-dibenzoic acid
Melting point 287 – 290° C.

Dithiodiacetic acid
Melting point 102 – 105° C.

-continued

| | | |
|---|---|---|
| (104) | H₃C—HC—S—S—CH—CH₃<br>　　　│　　　　　│<br>　　HOOC　　　COOH | 2,2'-Dithiodipropionic acid<br>Melting point 90 – 116° C. |
| (105) | H₃C—HC—S—S—CH—CH₃<br>　　　│　　　　　│<br>　　H₂C—H₂C　　CH₂—CH₂<br>　　　│　　　　　│<br>　　NaO₃S　　　SO₃Na | Disodium salt of 3,3'-dithiodibutane-1,1'-disulphonic acid (Manufacturing instructions C) |
| (106) | HOOC—HC—S—S—CH—COOH<br>　　　│　　　　　│<br>　HOOC—H₂C　　CH₂—COOH | Dithiodisuccinic acid<br>Melting point 171 – 173° C. |
| (107) | HOOC—⟨cyclohexane⟩—S—S—⟨cyclohexane⟩—COOH | 1,1'-Dithio-dicyclohexane-4,4'-dicarboxylic acid (Manufacturing instructions B) |
| (108) | H₂N　　　　　　NH₂<br>　│　　　　　　　│<br>HC—H₂C—S—S—CH₂—CH<br>　│　　　　　　　│<br>HOOC　　　　　COOH | L-Cystine |

In comparison experiments which are carried out in this way and in which the acidity of some substances is so compensated with 5% strength potassium hydroxide solution that the pH value of the developer solution remains constant, the results given in the table which follows are obtained. The two compounds

| | | |
|---|---|---|
| (109) | H₃C—CH—COOH<br>　　　│<br>　　　SH | (thiolactic acid) and |
| (110) | 　　　CH₃<br>　　　│<br>H₃C—C—COOH<br>　　　│<br>　　　SH | (α-mercaptoisobutyric acid) | are also included in the comparison. These compounds do indeed also display the desired clarity-preserving effect but are conspicuous by their extremely unpleasant odour, which is also transmitted to the developer solutions containing these substances and thus makes it virtually impossible to use these compounds. With the compounds, to be used according to the invention, of the formulae (102) to (108), on the other hand, virtually no troublesome odour arises.

TABLE

| | | State after | |
|---|---|---|---|
| Compound | g/l | 2 hours | 24 hours |
| (102) 2,2'-Dithiodibenzoic acid | 3.1 | clear, no sediment | clear, grey sediment |
| (103) Dithiodiacetic acid | 1.8 | clear, no sediment | clear, grey-black sediment |
| (104) 2,2'-Dithiodipropionic acid | 2.1 | clear, no sediment | slightly turbid, slight sediment |
| (105) Disodium salt of 3,3'-dithiodibutane-1,1'-disulphonic acid | 3.8 | clear, no sediment | clear, no sediment |
| (106) Dithiodisuccinic acid | 3.3 | clear, no sediment | turbid, grey sediment |
| (107) 1,1'-Dithio-dicyclohexane-4,4'-dicarboxylic acid | 3.2 | clear, no sediment | clear, no sediment |
| (108) L-Cystine | 2.4 | clear, no sediment | clear, slight sediment |
| (109) Thiolactic acid | 1.1 | clear, no sediment | slightly turbid, grey-black sediment |
| (110) α-Mercaptoisobutyric acid | 1.2 | clear, no sediment | clear, no sediment |

EXAMPLE 2

An aqueous monobath developer solution of the following composition is prepared:

Tetrasodium ethylenediaminetetraacetate: 2g/l
Anhydrous sodium sulphite: 60 g/l
Anhydrous sodium carbonate: 25 g/l
85% strength potassium hydroxide: 7 g/l
1-Phenyl-3-pyrazolidone: 1 g/l
Hydroquinone: 16 g/l
Anhydrous sodium thiosulphate: 70 g/l
Sodium salt of 2,2'-dithiodiethanesulphonic acid (Compound (111)): 1 g/l The melting point of the dithio compound is 134° to 136° C (guanidinium salt). The pH value of the solution is about 10.5.

10 exposed 9 cm × 12 cm sheet films are treated in succession, each for 8 minutes, at 24° C in 1 liter of this developer solution. A black-and-white photographic film of medium sensitivity is used. The pieces of film are then washed.

The developer solution used in this way is clear 2 hours after the treatment of the material has been concluded and no turbidity or deposition of a sediment can be observed even after 24 hours. A developer solution which had an identical composition, but without the 2,2'-dithiodiethanesulphonic acid, and was used in the same way is turbid and opaque 2 hours after use; it clears after 24 hours but a grey-black precipitate has settled out.

The dithio and trithio compounds which follow can also be added, in a concentration of 1 g/l, to the developer solution in place of the 2,2'-dithiodiethanesulphonic acid (Na salt) of the formula $$NaO_3S(CH_2)_2S—S(CH_2)_2SO_3Na \qquad (111)$$

Good results are also obtained with these compounds, that is to say even after 24 hours no sediment is observed in the developer solution used; the solution remains clear.

| | | |
|---|---|---|
| (112) | HOOC—⟨C₆H₄⟩—S—S—⟨C₆H₄⟩—COOH | 4,4'-Dithiodiphenyl-dicarboxylic acid<br>Melting point 338 – 341° C. |
| (113) | HOOC(CH₂)₂—S—S—(CH₂)₂COOH | 3,3'-Dithiodipropionic acid<br>Melting point 156 – 158° C. |
| (114) | HOOC(CH₂)₃—S—S—(CH₂)₃COOH | 4,4'-Dithiodibutyric acid<br>Melting point 109 – 111° C. |
| (115) | HOOC—C(CH₃)₂—S—S—C(CH₃)₂—COOH | 2,2'-Dithiodiisobutyric acid<br>Melting point 199 – 201° C. |
| (116) | HOOC—C(CH₃)₂—S—S—S—C(CH₃)₂—COOH | 2,2'-Trithiodiisobutyric acid<br>Melting point 173 – 175° C. |
| (117) | HOOC—C(CH₃)₂—CH₂—S—S—CH₂—C(CH₃)₂—COOH | Dithiodipivalic acid<br>Melting point 149 – 151° C. |
| (118) | HOOC—CH₂—C(CH₃)₂—S—S—C(CH₃)₂—CH₂—COOH | 3,3'-Dithio-bis-(3,3'-dimethyl)-propionic acid<br>Melting point 97 – 98° C. |
| (119) | HOOC—CH₂—CH(C₆H₅)—S—S—CH(C₆H₅)—CH₂—COOH | 3,3'-Dithio-bis-(3,3'-diphenyl)-propionic acid<br>Melting point 141 – 142° C. |
| (120) | HOOC—CH₂—CH(C₆H₄SO₂NH₂)—S—S—CH(C₆H₄SO₂NH₂)—CH₂—COOH | 3,3'-Dithio-bis-[3,3'-di-(4''-sulphamoylphenyl)]-propionic acid<br>Melting point 210 – 213° C. (decomposition) |
| (121) | HOOC—⟨pyrimidyl-NH₂⟩—S—S—⟨pyrimidyl-NH₂⟩—COOH | 4,4'-Diamino-2,2'-dithio-bis-[pyrimidyl-5,5'-dicarboxylic acid]<br>Melting point 250° C (decomposition) |
| (122) | HOOC—CH(CH₂COOH)—CH₂—S—S—CH₂—CH(CH₂COOH)—COOH | Dithiodiitamalic acid<br>Melting point 151 – 155° C. |
| (123) | HOOC—CH₂—CH(CH₂CH₃)—S—S—CH(CH₂CH₃)—CH₂—COOH | 3,3'-Dithiodivaleric acid (yellowish oil) |
| (124) | HOOC—CH(CH₃)—CH(CH₃)—S—S—CH(CH₃)—CH(CH₃)—COOH | 3,3'-Dithio-bis-[2-methyl]-butyric acid (yellowish oil) |
| (125) | NaOOC—CH₂—CH(HOOC—CH₂)—S—S—CH(CH₂COOH)—CH₂—COOH | Sodium salt of 3,3'-dithiodiglutaric acid<br>Melting point > 300° C. (monosodium salt) |
| (126) | HOOC—⟨cyclohexane(COOH)⟩—S—S—⟨cyclohexane(COOH)⟩—COOH | 4,4'-Dithio-bis-[cyclohexane-1,2-dicarboxylic acid<br>Melting point 110 – 135° C. |
| (127) | HOOCCH₂—⟨cyclopentyl⟩—S—S—⟨cyclopentyl⟩—CH₂COOH | 2,2'-Dithio-bis-(cyclopentyl)-acetic acid (colourless oil) |
| (128) | HOOCCH₂CH(furyl)—S—S—CH(furyl)—CH₂COOH | 3,3'-Dithio-bis-[3-(2'-furyl)]-propionic acid<br>Melting point 86 – 89° C. |

-continued

| | | |
|---|---|---|
| (129) | HOOC—CH₂—CH—S—S—CH—CH₂—COOH (with thienyl groups) | 3,3'-Dithio-bis-[3-(2'-thienyl)]-propionic acid<br>Melting point 149 – 150° C. |
| (130) | KOOC—CH₂—NH—CO—CH—S—S—CH—CO—NH—CH₂—COOK<br>          CH₃      CH₃ | Potassium salt of 2,2'-dithio-dipropionic acid (N,N'-carboxy-methyl)-amide.<br>Melting point > 300° C. |
| (131) | HOOC-(pyridyl)-S—S-(pyridyl)-COOH | 6,6'-Dithiodi-nicotinic acid<br>Melting point 247 – 249° C. (decomposition) |
| (132) | HOOC—CH₂—CH—S—S—CH—CH₂—COOH (with tolyl groups) | 3,3'-Dithio-bis-[3,3'-di-(4''-tolyl)]-propionic acid<br>Melting point 196 – 198° C. |
| (133) | HOOC—CH₂S-(phenyl)-S—S-(phenyl)-SCH₂—COOH | 4,4'-bis-(Carboxymethylmercapto)-diphenyl disulphide<br>Melting point 105 – 108° C. |
| (134) | HOOC-(phenyl)-CH₂—S—S—CH₂-(phenyl)-COOH | Dibenzyl-disulphide-4,4'-dicarboxylic acid<br>Melting point 278 – 280° C. (decomposition) |
| (135) | HOOC—CH₂—S—S—S—CH₂—COOH | 2,2'-Trithiodiacetic acid<br>Melting point 122 – 124° C. |

EXAMPLE 3

A photographic material for the silver dye-bleach process is manufactured on a pigmented cellulose acetate support using the cyan image dyestuff of the formula

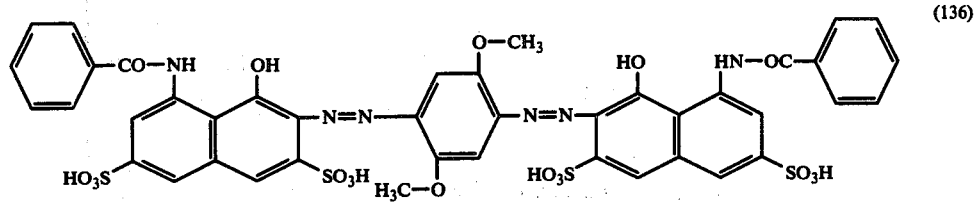

in the red-sensitised bottom-most layer, the magenta dyestuff of the formula

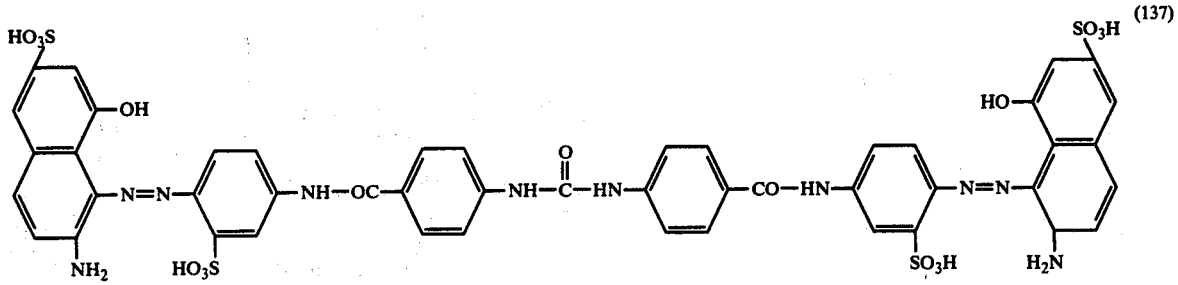

in the green-sensitised layer above this and the yellow dyestuff of the formula

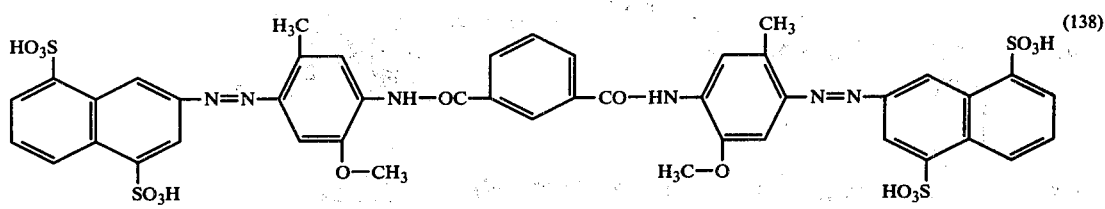

in a blue-sensitive layer which is located above the magenta layer.

The photographic material used is built up as follows (compare German Offenlegungsschriften Nos. 2,036,918 and 2,132,836):

Gelatine protective layer
Blue-sensitive, iodide-free AgBr emulsion
Yellow dyestuff (3) + blue-sensitive, iodide-free AgBr emulsion
Yellow filter: yellow Ag hydrosol (40 mg/m$^2$)
Green-sensitive AgBr/AgI emulsion
Magenta dyestuff (2) + green-sensitive AgBr/AgI emulsion
Intermediate layer (gelatine)
Cyan dyestuff (1) + red-sensitive AgBr/AgI emulsion
Red-sensitive AgBr/AgI emulsion
White opaque cellulose triacetate support
Gelatine backing The build-up of the layers makes it possible to correct the blue secondary colour densities of the cyan dyestuff and the magenta dyestuff by additional bleaching of the yellow image dyestuff as a function of the bleaching of the two other image dyestuffs (blue-sensitive layer which is iodide-free and contains the yellow dyestuff and the other colour layers which have an emulsion containing iodide). The layer containing nuclei is adjacent to the yellow dyestuff layer. It additionally contains a yellow light dyestuff and is separated from the magenta layer by a colourless layer of emulsion (green-sensitive emulsion layer which contains AgI and at the same time is the septum).

The layers of emulsion which contain iodide contain crystals with 2.6 mol % of silver iodide and 97.4 mol % of silver bromide. The image dyestuffs are used in a concentration such that their reflectance value is 2.0 in each case; the total silver content of the 22μ thick material is 2.0 g/m$^2$.

A coloured slide is copied onto this material in an enlarger. The exposed material is processed in accordance with the following instructions (French Patent Specification 2,247,755). The processing temperature is 30° C.

| 1. Silver-developing bath 3 minutes | | |
|---|---|---|
| Tetrasodium salt of ethylenediamine tetraacetic acid | 2 | g/l |
| 85% strength potassium hydroxide | 30 | g/l |
| Boric acid | 16 | g/l |
| Potassium metabisulphite | 26 | g/l |
| 1-Phenyl-3-pyrazolidone | 0.2 | g/l |
| Hydroquinone | 5 | g/l |
| Ascorbic acid | 10 | g/l |
| Benztriazole | 0.6 | g/l |
| Potassium bromide | 2 | g/l |
| Anhydrous sodium thiosulphate | 0.6 | g/l |
| 3,3'-Dithiodibutyric acid of the formula (101) | 1 | g/l |
| 2. Washing 1 minute | | |
| 3. Bleaching bath 5 minutes | | |
| Sulphamic acid | 100 | g/l |
| Sodium m-nitrobenzenesulphonate | 10 | g/l |
| 1-Thioglycerol | 1 | ml/l |
| Potassium iodide | 6 | g/l |
| 2,3,6-Trimethylquinoxaline | 2 | g/l |
| 4. Washing 1 minute | | |
| 5. Fixing bath 4 minutes | | |
| Ammonium thiosulphate | 250 | g/l |
| Potassium metabisulphate | 50 | g/l |
| 85% strength potassium hydroxide | 20 | g/l |
| 6. Washing 6 minutes | | |
| Total processing time 20 minutes | | |

The reflection copy which is obtained of the slide after drying is distinguished by accurate tonal rendering and by unadulterated colour rendering.

The effect of the addition of 3,3'-dithiodibutyric acid (Compound 101) is that the developer solution remains free from deposits of metallic silver over a relatively long period.

In place of compound (101), the compounds (102) to (135) can also be employed, in a corresponding amount, in the silver-developing baths with an equally good result.

What is claimed is:

1. Process for developing a photographic material, which contains a silver halide and has been exposed image-wise, using an aqueous preparation which contains (a) a developer for the silver halide, (b) a water-soluble solvent for the silver halide selected from the group consisting of thioethers, thioamides and salts of thiocyanic, sulphurous and thiosulphuric acid or mixtures of these compounds containing as one component a salt of sulphurous acid and (c) as a compounds which avoids the deposition of metallic silver, a compound of divalent sulphur in solution, wherein this sulphur compound corresponds to the formula

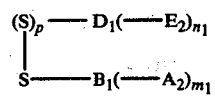

in which $B_1$ and $D_1$ each denote

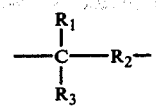

wherein $R_1$ is hydrogen, alkyl or hydroxyalkyl with 1 to 6 carbon atoms, phenyl, tolyl, cycloalkyl of 5 to 6 carbon atoms, or a five-membered to six-membered hetero-ring which contains 1 to 3 nitrogen atoms or 1 oxygen atom or 1 sulphur atom, or is a carboxylic acid group, $R_2$ is a direct bond or alkylene of 1 to 4 carbon atoms or phenylene, $R_3$ is hydrogen or alkyl of 1 to 2 carbon atoms or $B_1$ and $D_1$ each denote a cycloaliphatic radical of 5 to 6 carbon atoms, phenylene or a heterocyclic 5-membered or 6-membered ring and such ring fused with a further benzene ring, and the hetero-ring contains 1 to 3 nitrogen atoms, an oxygen atom or a sulphur atom, $m_1$ and $n_1$ each represent one of the numbers 1, 2 and 3, p represents 1 or 2 and $A_2$ and $E_2$ independently of one another each represent a radical of the formulae

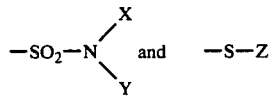

in which X and Y in each case are hydrogen or alkyl of at most 8 carbon atoms and is optionally substituted by hydroxyl groups, carboxylic acid groups or sulphonic acid groups and Y also represents a phenylsulphonic acid group, a lower alkylsulphonyl group or a phenylsulphonyl group and M represents a monovalent cation and Z has the meaning of X and Y with the exception of hydrogen.

2. Process according to claim 1, wherein the developer preparation contains a sulphur compound of the formula

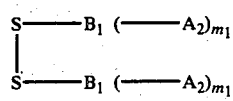

in which $m_1$, $A_2$ and $B_1$ have the meanings indicated in claim 1.

3. Process according to claim 2, wherein the developer preparation contains a sulphur compound of the formula

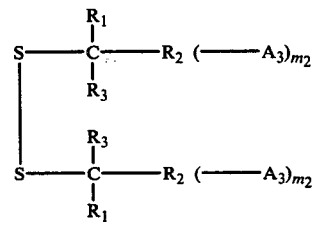

in which $m_2$ is 1 or 2, $R_1$ is hydrogen, alkyl or hydroxyzlkyl with at most 6 carbon atoms, phenyl, tolyl, cycloalkyl of 5 to 6 carbon atoms or a five-membered to six-membered heero-ring which contains 1 to 3 nitrogen atoms or 1 oxygen atom or 1 sulphur atom, or is a carboxylic acid group, $R_2$ is a direct bond, alkylene of 1 to 4 carbon atoms or phenylene, $R_3$ is hydrogen or alkyl of 1 to 2 carbon atoms and $A_3$ is a radical of the formulae —CO—O—M or —SO$_2$—O—M in which M is a monovalent cation.

4. Process according to claim 3, wherein the developer preparation contains a sulphur compound of the formula

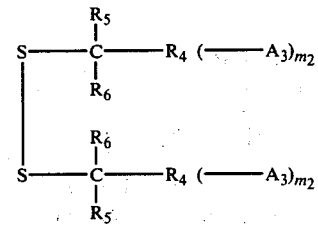

in which $m_2$ and $A_3$ have the meanings indicated in claim 5, $R_4$ is a direct bond or alkylene of 1 to 4 carbon atoms, $R_5$ is hydrogen, —CH$_3$, —CH$_2$OH, —COOH, —CH$_2$COOH, cyclopentyl, cyclohexyl, phenyl, tolyl, furyl or thienyl and $R_6$ is hydrogen, methyl or ethyl.

5. Process according to claim 3, wherein the developer preparation contains a sulphur compound of the formula

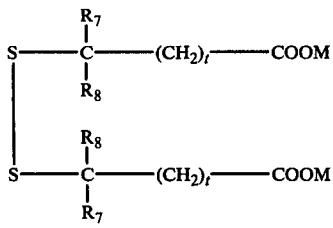

in which M is a monovalent cation, $t$ is an integer from 1 to 4, $R_7$ is hydrogen, —CH$_3$, —CH$_2$COOH, phenyl, p-tolyl or p-benzenesulphonamide and $R_8$ is hydrogen or —CH$_3$.

6. Process according to claim 3, wherein the developer preparation contains a sulphur compound of the formula

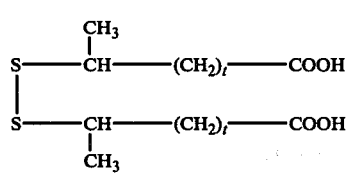

in which $t$ an integer from 1 to 4.

7. Process according to claim 6, wherein the developer preparation contains a sulphur compound of the formula

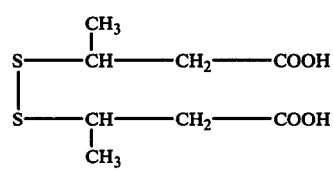

8. Process according to claim 3, wherein the developer preparation contains a sulphur compound of the formula

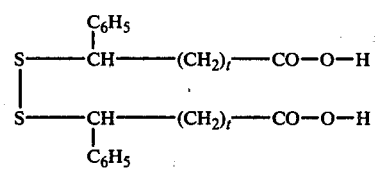

in which $t$ is an integer from 1 to 4.

9. Process according to claim 8, wherein the developer preparation contains a sulphur compound of the formula

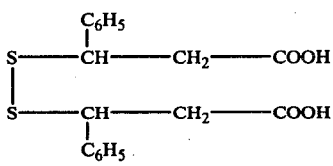

10. Process according to claim 2, wherein the developer preparation contains a sulphur compound of the formula

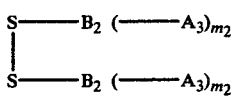

in which $m_2$ denotes 1 or 2, $B_2$ denotes a cycloaliphatic radical of 5 to 6 carbon atoms or phenyl or an N-aromatic-heterocyclic six-membered ring and $A_3$ denotes a radical of the formulae $$-CO-O-M \text{ and } -SO_2-O-M$$

in which M is a monovalent cation.

11. Process according to claim 10, wherein the developer preparation contains a sulphur compound of the formula

in which M is a monovalent cation and $B_3$ is cyclopentyl which in the 1-position is bonded to the sulphur atom and in the 5-position is bonded via —$CH_2$— to the C0 group, cyclohexyl which in the 1-position is bonded to the sulphur atom and in the 3-position or 4-position is bonded to the CO group, or phenyl which in the 1-position is bonded to the sulphur atom and in the 2-position or 4-position is bonded to the CO group.

12. Process according to claim 10, wherein the developer preparation contains a sulphur compound of the formula

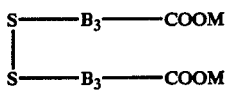

in which M is a monovalent cation and $B_4$ is optionally substituted pyrimidyl which in the 2-position is bonded to the sulphur atom and in the 5-position or 6-position is bonded to the CO group, or optionally substituted pyrindyl which in the 2-position is bonded to the sulphur atom and in the 4-position or 5-position is bonded to the CO group.

13. Process according to claim 1, wherein the developer preparation contains a sulphur compound of the formula

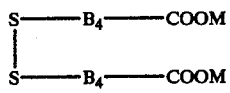

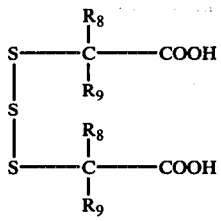

in which $R_8$ and $R_9$ independently of one another are hydrogen or methyl.

14. Process according to claim 1, wherein the developer preparation contains a sulphur compound of the formula

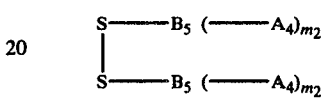

in which $A_4$ denotes a radical of the formulae —CO—O—M or $SO_2$—O—M, in which M is a monovalent cation and, $B_5$ denotes a cyclohexane radical which is bonded in the 1-position to the sulphur atom and in the 3- or 4-position to the —CO— group, and $m_2$ denotes the numbers 1 2.

15. Process according to claim 1, wherein the developer preparation contains a sulphur compound of the formula

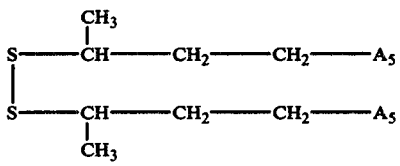

in which $A_5$ is a radical of the formula

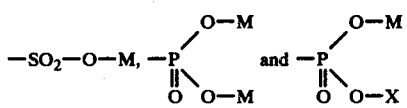

and M and has the meanings indicated in claim 1.

16. Process according to claim 7, wherein the developer preparation contains, as the solvent for the silver halide, a sulphite in a concentration of more than 20 g per liter, or a water soluble thiocyanate or thiosulphate.

17. Process according to claim 1, wherein silver dye-bleach material which has a composition suitable for reducing undesirable secondary colour densities is developed with a developer formulation of the indicated composition.

18. Preparation for developing a silver halide photographic material which has been exposed image-wise, which preparation contains (a) a developer substance for the silver halide, (b) a water-soluble solvent for the silver halide and (c) a compound of divalent sulphur in solution, wherein this sulphur compound corresponds to the formula

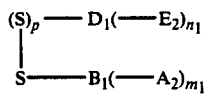

in which $B_1$ and $D_1$ each denote

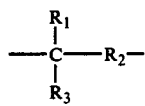

wherein $R_1$ is hydrogen, alkyl or hydroxyalkyl with 1 to 6 carbon atoms, phenyl, tolyl, cycloalkyl of 5 to 6 carbon atoms or a five-membered to six-membered hetero-ring which contains 1 to 3 nitrogen atoms or 1 oxygen atom or 1 sulphur atom, or is a carboxylic acid group, $R_2$ is a direct bond or alkylene of 1 to 4 carbon atoms or phenylene, $R_3$ is hydrogen or alkyl of 1 to 2 carbon atoms or $B_1$ and $D_1$ each denote a cycloaliphatic radical of 5 to 6 carbon atoms, phenylene or a heterocyclic 5-membered or 6-membered ring and such ring fused with a further benzene ring, and the hetero-ring contains 1 to 3 nitrogen atoms, an oxygen atom or a sulphur atom, $m_1$ and $n_1$ each represents one of the numbers 1, 2 and 3, $p$ represents 1 or 2 and $A_2$ and $E_2$ independently of one another each represent a radical of the formulae

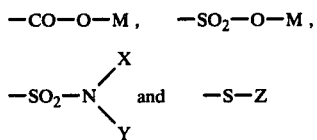

in which X and y in each case are hydrogen or alkyl of at most 8 carbon atoms and is optionally substituted by hydroxyl groups, carboxylic acid groups or sulphonic acid groups and Y also represents a phenylsulphonic acid group, a lower alkylsulphonyl group or a phenylsulphonyl group and M represents a monovalent cation and Z has the the meaning of X and Y with the exception of the hydrogen.

* * * * *

UNITED STATES PATENT AND TRADEMARK OFFICE
CERTIFICATE OF CORRECTION

PATENT NO. : 4,141,734

DATED : February 27, 1979

INVENTOR(S) : John Lenoir et al.

Page 1 of 2

It is certified that error appears in the above-identified patent and that said Letters Patent are hereby corrected as shown below:

```
Column 5, line 39, "donote" should be --denote--.
Column 6, line 34, "siulphides" should be --sulphides--
Column 7, line 32, delete "d" before "4-chlorocin-".
Column 7, line 35, "methylendioxy..." should be
     --methylene...--.
Column 7, line 51, "3,3" should be --3,3'--.
Column 7, line 59, "...phonamide" should be --...phonamido--.
Column 7, line 61, "-bis(2"..." should be -- -bis-(2"...--.

Column 8, line 65, insert "in" before "the 3-".
Column 9, line 18, "indicating" should be --indicated--.
column 9, line 33, "The" should be --These--.
Column 9, line 44, "ester" should be --esters--.
Column 10, line 40, "The" should be --This--.
```

UNITED STATES PATENT AND TRADEMARK OFFICE
CERTIFICATE OF CORRECTION

PATENT NO. : 4,141,734

DATED : February 27, 1979

INVENTOR(S) : John Lenoir et al.

It is certified that error appears in the above-identified patent and that said Letters Patent are hereby corrected as shown below:

Column 11, line 8, "atni-" should be --anti--.
Column 11, line 35, "fee" should be --free--.

Column 12, line 43, "trearted" should be --treated--.
Column 19, line 37 insert "filter" before "dyestuff"
Column 20, line 39, "compounds" should be --compound--.
Column 21, line 47, "heero" should be --hetero--.
Column 24, line 26 delete "and" before "$B_5$".
Column 24, line 30 insert "or" after "1".
Column 26, line 15 "y" should be --Y--.
Column 26, line 23 delete "the" before "hydrogen.

Signed and Sealed this

Seventeenth Day of July 1979

[SEAL]

Attest:

LUTRELLE F. PARKER

*Attesting Officer*     *Acting Commissioner of Patents and Trademarks*